(12) United States Patent
Fitzgerald et al.

(10) Patent No.: US 7,917,378 B2
(45) Date of Patent: Mar. 29, 2011

(54) SYSTEM FOR PROCESSING HEALTHCARE CLAIM DATA

(75) Inventors: David Fitzgerald, West Grove, PA (US);
Brian Lucas, Springfield, PA (US);
Greg Long, Conshohocken, PA (US);
David Hiebert Klassen, Sr., Paoli, PA (US); John Hunter, North Wales, PA (US); Jon Zimmerman, Pitman, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 3170 days.

(21) Appl. No.: 10/247,980

(22) Filed: Sep. 20, 2002

(65) Prior Publication Data

US 2003/0191665 A1    Oct. 9, 2003

Related U.S. Application Data

(60) Provisional application No. 60/371,027, filed on Apr. 9, 2002, provisional application No. 60/384,487, filed on May 31, 2002.

(51) Int. Cl.
*G06Q 40/00* (2006.01)
*G06Q 10/00* (2006.01)
*G06Q 50/00* (2006.01)

(52) U.S. Cl. .................................. 705/4; 705/2
(58) Field of Classification Search .................. 705/3, 4
See application file for complete search history.

(56) References Cited

U.S. PATENT DOCUMENTS

| 4,858,121 A | 8/1989 | Barber et al. | 364/406 |
| 5,253,164 A * | 10/1993 | Holloway et al. | 705/2 |
| 5,301,105 A | 4/1994 | Cummings, Jr. | 705/2 |
| 5,359,509 A * | 10/1994 | Little et al. | 705/2 |
| 5,517,405 A | 5/1996 | McAndrew et al. | |

(Continued)

FOREIGN PATENT DOCUMENTS

JP    11161704 A    6/1999

OTHER PUBLICATIONS

International Search Report.

(Continued)

*Primary Examiner* — Gerald J. O'Connor
*Assistant Examiner* — Sheetal R Rangrej
(74) *Attorney, Agent, or Firm* — Alexander J Burke

(57) ABSTRACT

A claim pre-processing system employs trial adjudication to improve claim accuracy prior to claim submission to a healthcare payer institution or other entity. A system processes claim data related to provision of healthcare to a patient The system includes a claim data collator for collating data related to a claim for a particular patient for submission to a payer and a source of rules for use in processing collated claim data. A pre-processor submits the collated claim data for processing using the rules to validate the collated claim data is in condition for processing to initiate generation of payment. A claim processor submits the collated claim data to a payer, in response to successful validation by the pre-processor. A rules processor processes acquired claim data to identify a condition triggering application of a different set of rules for determining validity of an individual claim element. The pre-processor re-submits amended collated claim data for processing using the rules to validate the collated claim data is in condition for processing to initiate generation of payment, the amended collated claim data being received in response to unsuccessful validation using the rules.

28 Claims, 12 Drawing Sheets

U.S. PATENT DOCUMENTS

| | | | |
|---|---|---|---|
| 5,915,241 A * | 6/1999 | Giannini | 705/2 |
| 5,924,074 A | 7/1999 | Evans | 705/3 |
| 5,991,733 A | 11/1999 | Aleia et al. | |
| 6,208,973 B1 | 3/2001 | Boyer et al. | |
| 6,263,330 B1 | 7/2001 | Bessette | 707/4 |
| 6,282,531 B1 | 8/2001 | Haughton et al. | |
| 6,343,271 B1 * | 1/2002 | Peterson et al. | 705/2 |
| 2001/0034618 A1 | 10/2001 | Kessler et al. | |
| 2002/0019754 A1 | 2/2002 | Peterson et al. | 705/4 |
| 2002/0032583 A1 | 3/2002 | Joao | 705/2 |
| 2002/0032584 A1 | 3/2002 | Doctor et al. | |
| 2002/0035488 A1 | 3/2002 | Aquila et al. | |
| 2002/0147867 A1 | 10/2002 | Satlow | 710/100 |
| 2003/0055679 A1 | 3/2003 | Soll et al. | 705/2 |
| 2003/0069760 A1 | 4/2003 | Gelber | 705/4 |
| 2003/0158760 A1 * | 8/2003 | Kannenberg | 705/4 |

OTHER PUBLICATIONS deNovis, Inc. http://www.denovis.com/product/claims.htm.

* cited by examiner

```
┌─ Session_a-RUMBA Mainframe Display ──────────────────────────────── _ □ × ┐
│ File  Edit  View  Connection  Transfer  Options  Tools  Help              │
│ [icons...]                                                                 │
│                                                                            │
│ 06/14/02 12:28PM         EGL  SINGLE  GENERAL  HOSPITAL        UB92  REV-CODES  SECTION
│ PAT# 2969    NAME: MORETHANTWENTYSIX,  TES AREA:  ACLMED       SEX/DOB:  M  01/11/1967
│                                                                                    ──420
│   Entire-List ======================================  CLAIMID# 10129608 ========
│
│ SEQ#   I/D     REVCD        TYPE   SVC DATE     UNITS/DAYS    RATE / PROC       TOTL CHARGES    NON - CVD CHRG
│ ---    ---     -----        ----   --------     ----------    -----------       ------------    --------------
│   1            540            A    04/29/02         2         A0425
│                AMBULANCE
│   2            250            C    04/29/02         1         27301                2000.00
│                PHARMACY                                       DRAIN THIGH / KNEE LESION
│   3            250            C    04/29/02         1         27305
│                PHARMACY                                       INCISE THIGH TENDON & FASCIA
│
│ ** ERROR:   Revenue Code #1 invalid < 540 >
│ ** ERROR:   Acom Rate/Ancil Proc Cd #1 not in format n.nn- < A0425 >
│    WARNING: Revenue Code #1 present < 540 >
│    WARNING: Accomodatn/Ancillary Ind #1 present < A >
│    WARNING: Acom Days/Ancil Units #1 present < 2 >
│ &AMBULANC   &MOTORVEH      &ALCOHOL         &PAYOR       &VOCS         &PACEMAKE       G10306A
│ &PATDATA    &EXIT          &CANCEL          &ERRLIST     &MENU         &MEDICAL        G50312A
│ &APCDTL     &CLEAR         &ALLMSG          &PREVAREA                                  G20306A
│                                                         ACTION ==>                    G20303A
│                                                                                        G20318A
│
│ [Ready]                    [Running]          [APL] [NUMFLD] [SNA1@120] [OVR] [CAP] [NUM] [W] [9,13] [12:32:28 PM]
└────────────────────────────────────────────────────────────────────────────┘
       402 ↗    404 ↗    406 ↗
```

```
session_a-RUMBA Mainframe Display                                          _ □ ×
File  Edit  View  Connection  Transfer  Options  Tools  Help
[toolbar icons]

06/14/02  12:35PM               EGL   SINGLE   GENERAL   HOSPITAL           CLAIM ERROR LIST
PAT#  2969       NAME:  MORETHANTWENTYSIX,  TES AREA:   ACLMED       UB92   SEX/DOB:  M    01/11/1967 ─── 420
                                                                            ================
       Entire-List  ======   UB92 CLAIM MANAGER  ===========        CLAIMID#  10129608 ────────
                                                                                                 SHOW CLEARED ERRS: N
SEQ#   SEL   ERRCD/LVL   I/D   MESSAGE TEXT
  1          G10306  E    6R   Revenue Code #1 invalid  < 540 >
  2          G50312  E    6R   Acom Rate/Ancil Proc  Cd #1 not in format n.nn- < A0425 >
  3          B10165  H    3P   Insured Last Name #1 missing
  4          G20303  W    6R   Accomodation/Ancillary Ind #1 present < A >
  5          G20306  W    6R   Revenue Code #1 present < 540 >
  6          G20312  W    6R   Acom Rate/Ancil Proc Cd #1 present < A0425 >
  7          G20318  W    6R   Acom Days/Ancil Units #1 present <       2 >

&REMARKS     &REPLICAT    &PACEMAKE    &ALCOHOL    &REHAB      &END
&AMBULANC    &CHARGES     &VOCS        &PAYOR      &MEDICAL    &MOTORVEH
&CANCEL      &MENU        &EXIT        &PATDATA    ACTION ==>

Ready                              Running             APL  NUMFLD  SNA1@120  OVR  CAP  NUM  W  32.66  12:4:31 PM
```

| | ERROR CODE | TEXT | COMMENTS | RULE CATEGORY |
|---|---|---|---|---|
| 700 | SA0021 | CAUSEOFINJURY PRESENT, NO PLACEOFINJURY | THE PAYER HAS DECLARED A RULE THAT: IF A CLAIM CONTAINS A CAUSE OF INJURY CODE, THEN IT MUST ALSO CONTAIN A PLACE OF INJURY CODE." THE PRE-PROCESSOR IS ISSUING A WARNING MESSAGE BECAUSE IT HAS DETECTED THAT A CLAIM VIOLATES THIS RULE, BECAUSE IT CONTAINS A CAUSE OF INJURY CODE, BUT NO PLACE OF INJURY CODE. | 1 |
| 703 | SC0020 | SVCDT - OCE OUT OF RANGE | THIS IS AN OUTPATIENT CODE EDIT (OCE). THE PRE-PROCESSOR IS ISSUING A WARNING MESSAGE BECAUSE A SERVICE DATE (SVCDT) IS NOT WITHIN THE RANGE OF EFFECTIVE DATES OF THE PROSPECTIVE PAYMENT SYSTEM. (E.G., THE SERVICE DATE IS PRIOR TO AUGUST, 2000.) | 2 |
| 705 | SC0021 | SVCDT - OCE NOT IN STMT PERIOD | THIS IS AN OUTPATIENT CODE EDIT (OCE). THE PRE-PROCESSOR IS ISSUING A WARNING MESSAGE BECAUSE A SERVICE DATE IS NOT IN THE RANGE DEFINED BY THE FROM - THROUGH SERVICE DATES ON THE CLAIM. | 2 |
| 707 | SC0008 | HCPCS- OCE NON-COVERED PROCEDURE | THIS IS AN OUTPATIENT CODE EDIT (OCE). THE PRE-PROCESSOR IS ISSUING A WARNING MESSAGE BECAUSE CERTAIN HOSPITAL PROCEDURE CODES ARE NOT CONSIDERED TO BE "COVERABLE" UNDER OPPS (AN OUTPATIENT PROSPECTIVE PAYMENT SYSTEM). THE PRE-PROCESSOR HAS DETECTED A PROCEDURE THAT HAS A "NON-COVERED" SERVICE INDICATOR. | 2 |
| 709 | SC0019 | ADMDT- OCE INVALID DATE | THIS IS AN OUTPATIENT CODE EDIT (OCE). THE PRE-PROCESSOR IS ISSUING A WARNING MESSAGE BECAUSE THE ADMISSION DATE FIELD (ADMDT) IN A CLAIM CONTAINS A VALUE THAT CANNOT BE INTERPRETED AS A VALID DATE. | 1 |
| 711 | SC0003 | DIAG/ PATBIRTHDT/AGE - OCE CONFLICT | THIS IS AN OUTPATIENT CODE EDIT (OCE). OCE CONTAINS RULES COLLECTIVELY KNOWN AS THE CCI (CORRECT CODING INITIATIVE). THE CCI IDENTIFIES CONDITIONS WHERE CERTAIN PROCEDURE CODES, DIAGNOSIS CODES, OR COMBINATIONS OF THESE CODES ARE NOT ALLOWED. THE PRE-PROCESSOR IS ISSUING A WARNING MESSAGE BECAUSE A DIAGNOSIS CODE IS FOUND IN A CLAIM THAT CANNOT BE APPLIED TO A PATIENT OF THE SPECIFIED AGE. | 1 OR 2 |
| 713 | SC0004 | DIAG/PATSEX - OCE CONFLICT | THIS IS AN OUTPATIENT CODE EDIT (OCE). OCE CONTAINS RULES COLLECTIVELY KNOWN AS THE CCI (CORRECT CODING INITIATIVE). THE CCI IDENTIFIES CONDITIONS WHERE CERTAIN PROCEDURE CODES, DIAGNOSIS CODES, OR COMBINATIONS OF THESE CODES ARE NOT ALLOWED. THE PRE-PROCESSOR IS ISSUING A WARNING MESSAGE BECAUSE A DIAGNOSIS CODE HAS BEEN FOUND IN A CLAIM THAT CANNOT BE APPLIED TO A PATIENT OF THE SPECIFIED SEX. | 1 OR 2 |
| 715 | SC0005 | HCPCS/PATSEX - OCE CONFLICT | THIS IS AN OUTPATIENT CODE EDIT (OCE). OCE CONTAINS RULES COLLECTIVELY KNOWN AS THE CCI (CORRECT CODING INITIATIVE). THE CCI IDENTIFIES CONDITIONS WHERE CERTAIN PROCEDURE CODES, DIAGNOSIS CODES, OR COMBINATIONS OF THESE CODES ARE NOT ALLOWED. THE PRE-PROCESSOR IS ISSUING A WARNING MESSAGE BECAUSE A PROCEDURE CODE (HCPCS) IS FOUND IN THE CLAIM THAT CANNOT BE APPLIED TO A PATIENT OF THE SPECIFIED SEX. | 1 OR 2 |
| 717 | SA0157 | OC DT GT ADMDT | OCCURRENCE CODES (OC) ARE CODED ON CLAIMS TO REPORT THAT CERTAIN EVENTS HAVE OCCURRED. FOR EACH OCCURRENCE CODE AN OCCURRENCE DATE (OC DT) IS ALSO TO BE SPECIFIED. AS AN EXAMPLE, AN OCCURRENCE CODE OF 41 (PREADMISSION TEST) IS ENTERED ON THE CLAIM. THE PRE-PROCESSOR IS ISSUING A WARNING MESSAGE BECAUSE THE OCCURRENCE DATE ASSOCIATED WITH OCCURRENCE CODE 41 IS GREATER THAN (GT) - I.E., FALLS AFTER - THE ADMISSION DATE (ADMDT). | 1 |
| 719 | SA0152 | INVALID I/P REVCD | THE CLAIM IS FOR AN INPATIENT (I/P). THE PRE-PROCESSOR IS ISSUING A WARNING MESSAGE BECAUSE ONE OF THE REVENUE CODE (REVCD) FIELDS ON THE CLAIM CONTAINS A VALUE THAT IS NOT A VALID INPATIENT REVENUE CODE. | 1 |
| 721 | SA0147 | MAMMO REVCD-MUST BE BILLED SEPARATELY | THE PRE-PROCESSOR IS ISSUING A WARNING MESSAGE BECAUSE IT DETECTED A MAMMOGRAM REVENUE CODE ON A CLAIM ALSO CONTAINING OTHER CHARGES. MAMMOGRAM SERVICES ARE TO BE CLAIMED SEPARATELY. | 1 |

FIG. 7

Patient record
```
           PATIENT_RECORD,
800 ─────── PACKET_ID        CHAR(5),     /* claim packet number              0 */
802 ─────── SECTION_ID       CHAR(8),     /* section id - "PATIENT"           5 */
804 ─────── SEQ_NUM          PIC'(4)9',   /* record sequence number          13 */
806 ─────── PAT_LAST_NM      CHAR(20),    /* PATIENT LAST NAME      20 - 4   17 */
808 ─────── PAT_FIRST_NM     CHAR(12),    /* PATIENT FIRST NAME     20 - 5   37 */
810 ─────── PAT_MIDDL_I      CHAR(1),     /* PATIENT MIDDLE INITIAL 20 - 6   49 */
            PAT_ADDR_1       CHAR(25),    /* PATIENT ADDRESS 1      20 - 12  50 */
            PAT_ADDR_2       CHAR(25),    /* PATIENT ADDRESS 2      20 - 13  75 */
            PAT_CITY         CHAR(15),    /* PATIENT CITY           20 - 14 100 */
            PAT_STATE        CHAR(2),     /* PATIENT STATE          20 - 15 115 */
            PAT_ZIP          CHAR(9),     /* PATIENT ZIP            20 - 16 117 */
            PAT_COUNTRY_CD   CHAR(2),     /* PATIENT COUNTRY CODE   N404    126 */
            PAT_COUNTY       CHAR(2),     /* PATIENT COUNTY CODE    25 - 22 128 */
            PAT_PHONE        CHAR(14),    /* phone# aaaxxxxxxx Ext4 26 - 4  130 */
            PAT_SEX          CHAR(1),     /* PATIENT SEX            20 - 7  144 */
            PAT_DOB          CHAR(8),     /* PATIENT BIRTH DATE     20 - 8  145 */
            PAT_SOC_SEC      CHAR(9),     /* PATIENT SOCIAL SEC#    86 - 8  153 */
            PAT_MARTL        CHAR(1),     /* PATIENT MARITAL STS    20 - 9  162 */
            PAT_RACE         CHAR(2),     /* PATIENT RACE           25 - 13 163 */
            PAT_ETHNIC       CHAR(1),     /* PATIENT ETHNICITY      25 - 14 165 */
            EMP_INFO(4),
                EMP_NAME     CHAR(30),    /* EMPLOYER NAME          21 - 4&11 166 */
                EMP_ADDR     CHAR(25),    /* EMPLOYER ADDRESS       21 - 5&12 196 */
                EMP_CITY     CHAR(15),    /* EMPLOYER CITY          21 - 6&13 221 */
                EMP_STATE    CHAR(2),     /* EMPLOYER STATE         21 - 7&14 236 */
                EMP_ZIP      CHAR(9),     /* EMPLOYER ZIP           21 - 8&15 238 */
                EMP_STS      CHAR(1),     /* EMPLOYMENT STAT        21 - 9&16 247 */
            MR_NUMBER        CHAR(17),    /* M/R NUMBER             20 - 25 494 */
            STMT_FRM_DT_1D   CHAR(8),     /* STATEMENT FROM DT      20 - 19 511 */
            STMT_TO_DT_1D    CHAR(8),     /* STATEMENT TO DATE      20 - 20 519 */
            ADM_DATE         CHAR(8),     /* ADMIT DATE             20 - 17 527 */
            ADM_HOUR         CHAR(2),     /* ADMIT HOUR             20 - 18 535 */
            ADM_MIN          CHAR(2),     /* ADMIT MIN                      537 */
            ADM_TYPE         CHAR(1),     /* ADMIT TYPE             20 - 10 539 */
            ADM_SOURCE       CHAR(1),     /* ADMIT SOURCE           20 - 11 540 */
            ADM_SCHED        CHAR(1),     /* SCHED/UNSCHED ADM      25 - 15 541 */
            DSC_DATE         CHAR(8),     /* DISCHARGE DATE         25 - 4  542 */
            DSC_HOUR         CHAR(2),     /* DISCHARGE HOUR         20 - 22 550 */
            DSC_MIN          CHAR(2),     /* DISCHARGE MIN                  552 */
            STATE_DSC_STS    CHAR(2),     /* STATE DSC STATUS       25 - 9  554 */
```

FIG. 8

Medical record

```
           MEDICAL_RECORD,
900 ──────PACKET_ID      CHAR(5),      /* claim packet number              0 */
902 ──────SECTION_ID     CHAR(8),      /* section id - "MEDICAL"           5 */
904 ──────SEQ_NUM        PIC'(4)9',    /* record sequence number          13 */
906 ──────ADM_DIAG       CHAR(7),      /* ADMIT DIAGNOSIS CD    70 - 25   17 */
908 ──────PRM_DIAG       CHAR(7),      /* PRIMARY DIAG CD       70 - 4    24 */
910 ──────OTHER_DIAG(14),
           DIAG_CD       CHAR(7),      /* DIAG CODES       70 - 5:12/79 - 4:9    31 */
           DIAG_IND      CHAR(1),      /* OTH DIAG IND          79 - 10:23       38 */
           DIAG_ANES     CHAR(1),      /* OTH DIAG AFTR ANES    79 - 25:38       39 */
           PRN_PROC_CD   CHAR(7),      /* PRIN PROC             70 - 13         157 */
           PRN_PROC_DT   CHAR(8),      /* PRIN DATE             70 - 14         164 */
           OTHER_PROC(14),
              PROC_CODE  CHAR(7),      /* PROC CDS         70 - 15:23/79 - 4:20 172 */
              PROC_DATE  CHAR(8),      /* PROC DTS         70 - 16:24/79 - 5:21 179 */
           CAUSE_OF_INJ  CHAR(7),      /* EXT CAUSE OF INJ      70 - 26         382 */
           PLACE_OF_INJ  CHAR(7),      /* PLACE OF INJURY       79 - 39         389 */
```

FIG. 9

Payor record

```
       PAYOR_DATA_AREA,
920 ─── PACKET_ID      CHAR(5),    /* claim packet number              0 */
922 ─── SECTION_ID     CHAR(8),    /* section id - "PAYOR"             5 */
924 ─── SEQ_NUM        PIC'(4)9',  /* record sequence number          13 */
926 ─── SRC_OF_PAYMT   CHAR(2),    /* SOURCE OF PAYMENT CD    30 - 4  17 */
928 ─── PAYR_ID        CHAR(5),    /* PAYOR ID (PLN CD)       30 - 5  19 */
930 ─── PAYR_SUB_ID    CHAR(4),    /* PAYOR SUB ID            30 - 6  24 */
        INS_ID         CHAR(20),   /* CERIF/POLICY#/SS# . .   30 - 7  28 */
        PAYR_NAME      CHAR(30),   /* PAYOR NAME              30 - 8  48 */
        PLN_GRP_ID     CHAR(17),   /* INS/BLC/COM GRP ID      30 - 10 78 */
        PLN_GRP_NAME   CHAR(25),   /* INSURED'S GROUP NM      30 - 11 95 */
        PLN_ADDR_1     CHAR(25),   /* INS PLAN ADDRESS 1      35 - 15 120 */
        PLN_ADDR_2     CHAR(25),   /* INS PLAN ADDRESS 2      35 - 16 145 */
        PLN_CITY       CHAR(15),   /* INS PLAN CITY           35 - 17 170 */
        PLN_STATE      CHAR(2),    /* INS PLAN STATE          35 - 18 185 */
        PLN_ZIP        CHAR(9),    /* INS PLAN ZIP            35 - 19 187 */
        PLN_PHONE      CHAR(14),   /* phone# aaaxxxxxxx Ext4  86 - 11 196 */
        PRM_PAYR_CD    CHAR(1),    /* PRIM PAYOR CD           30 - 9  210 */
        INSRD_LNM      CHAR(20),   /* INSURED'S LST NAME      30 - 12 211 */
        INSRD_FNM      CHAR(12),   /* INSURED'S FRST NAM      30 - 13 231 */
        INSRD_MI       CHAR(1),    /* INSURED'S MIDDL I       30 - 14 243 */
        INSRD_SEX      CHAR(1),    /* INSURED'S SEX           30 - 15 244 */
        INSRD_ADDR_1   CHAR(25),   /* INSURED'S ADDR 1        31 - 4  245 */
        INSRD_ADDR_2   CHAR(25),   /* INSURED'S ADDR 2        31 - 5  270 */
        INSRD_CITY     CHAR(15),   /* INSURED'S CITY          31 - 6  295 */
        INSRD_STATE    CHAR(2),    /* INSURED'S STATE         31 - 7  310 */
        INSRD_ZIP      CHAR(9),    /* INSURED'S ZIP           31 - 8  312 */
        INSRD_DOB      CHAR(8),    /* INSURED'S D-O-B         DGM02   321 */
        INSRD_CNTRY    CHAR(2),    /* INSURED'S CNTRY CD      N404    329 */
        PAT_REL_INS    CHAR(2),    /* PAT REL TO INSRD        30 - 18 331 */
        PAT_TO_INS_837 CHAR(2),    /* REL TO INS 837 TRAN     30 - 18 333 */
        EMPL_NAME      CHAR(30),   /* EMPLOYER NAME           31 - 9  335 */
        EMPL_ADDR      CHAR(25),   /* EMPLOYER ADDRESS        31 - 10 365 */
        EMPL_CITY      CHAR(15),   /* EMPLOYER CITY           31 - 11 400 */
        EMPL_STATE     CHAR(2),    /* EMPLOYER STATE          31 - 12 415 */
        EMPL_ZIP       CHAR(9),    /* EMPLOYER ZIP            31 - 13 417 */
        EMPL_PHONE     CHAR(14),   /* EMPLOYER PHONE          86 - 10 426 */
        EMPL_STS       CHAR(1),    /* EMPLOYMENT STATUS       30 - 19 440 */
        RELS_OF_INFO   CHAR(1),    /* RELEASE OF INFO         30 - 16 441 */
```

FIG. 10

Charge record

```
            CHARGE_RECORD,
940 ────PACKET_ID       CHAR(5),     /* claim packet number                    0 */
942 ────SECTION_ID      CHAR(8),     /* section id - "CHARGES"                 5 */
944 ────SEQ_NUM         PIC'(4)9',   /* record sequence number                13 */
946 ────ACMD_ANC_ID     CHAR(1),     /* "A" - Accomodation Rates              17 */
                                     /* "C" - CPT-4 Codes                        */
                                     /* "I" - ICD9 Codes                         */
948 ────REV_CODE        CHAR(4),     /* ACMD/ANCL REV CD      50 - 4/60/61    18 */
950 ────SERV_DATE       CHAR(8),     /* ANCIL SRVC DATE           61 - 9      22 */
         PROC_OR_ICD9   CHAR(11),    /* HCPCS code                   60/61    30 */
         MOD1           CHAR(2),     /* modifier 1                            41 */
         MOD2           CHAR(2),     /* modifier 2                            43 */
         MOD3           CHAR(2),     /* modifier 3                            45 */
         MOD4           CHAR(2),     /* modifier 4                            47 */
         ACMD_RATE      PIC'(6)z9v.99-', /* ACM RATE               50 - 5     49 */
         FORM_LOC_49    CHAR(4),     /* FORM LOCATOR 49       50 - 9/60/61    60 */
         UNITS_DAYS     PIC'(3)z9v.99-', /* ACM DYS/ANC UNTS       50/60/61   64 */
         TOT_CHGS       PIC'(7)z9v.99-', /* ACMD TOT CHGS         50 - 7/60/61 72 */
         NON_CVD_CHGS   PIC'(7)z9v.99-', /* ACM NON COVD          50 - 8/60/61 84 */
```

FIG. 11

Occur Code record

```
            OCCUR_CODE_RECORD,
960 ────PACKET_ID       CHAR(5),     /* claim packet number                    0 */
962 ────SECTION_ID      CHAR(8),     /* section id - "OCURCODE"                5 */
964 ────SEQ_NUM         PIC'(4)9',   /* record sequence number                13 */
966 ────OCCUR_CODE      CHAR(4),     /* OCCURRENCE CODE                       17 */
968 ────DATE            CHAR(8),     /* OCCURRENCE DATE                       21 */
```

FIG. 12

Span Code record

```
         SPAN_CODE_RECORD,
980 ———PACKET_ID      CHAR(5),    /* claim packet number      0 */
982 ———SECTION_ID     CHAR(8),    /* section id - "SPANCODE"  5 */
984 ———SEQ_NUM        PIC'(4)9',  /* record sequence number  13 */
986 ———SPAN_CODE      CHAR(4),    /* SPAN CODE               17 */
988 ———FROM_DATE      CHAR(8),    /* START DATE              21 */
990 ———TO_DATE        CHAR(8),    /* END DATE                29 */
```

FIG. 13

Cond Code record.txt

```
         COND_CODE_RECORD,
830 ———PACKET_ID      CHAR(5),    /* claim packet number      0 */
832 ———SECTION_ID     CHAR(8),    /* section id - "CONCODE"   5 */
834 ———SEQ_NUM        PIC'(4)9',  /* record sequence number  13 */
836 ———COND_CODE      CHAR(4),    /* CONDITION CODE          17 */
```

FIG. 14

# SYSTEM FOR PROCESSING HEALTHCARE CLAIM DATA

This is a non-provisional application of provisional application Ser. No. 60/371,027 by D. Fitzgerald et al. filed Apr. 9, 2002 and of provisional application Ser. No. 60/384,487 by D. Fitzgerald et al. filed May 31, 2002.

FIELD OF THE INVENTION

This invention concerns a system and user interface for acquiring, validating and processing claim data for payment for provision of services to patients by a healthcare provider, for example.

BACKGROUND OF THE INVENTION

An important function performed by healthcare providers (such as hospitals, clinics or physicians) is the sending of claims to healthcare payer institutions to obtain reimbursement for provision of services to a patient. These claims may be in electronic or paper format. Paper claims typically go through a data entry process that converts them to an electronic format. The entered electronic claims are usually sorted, indexed and archived. Each claim is processed in a payer institution adjudication system. The payer adjudication system interprets the claim data and determines whether or not the claim is to be paid in full, partially paid or denied. This adjudication process may be fully automated, partially automated, or manual. The results of claim adjudication may include the issuance of a check and an explanation of benefits (EOB) to the insured and healthcare provider, or a request to send additional information. The process of reviewing claims is labor-intensive and error-prone.

Known adjudication systems help payers and providers streamline their claims payment and medical case management processes. A typical adjudication system employed by a payer institution, may use high speed scanning equipment and optical character recognition software to translate paper claims into electronic data. The electronic claim data is processed by rule based software to interpret the claim data for any conflicts. Conflicts are usually reported to a user either as an online claim image with areas of concern highlighted, or as a report. A typical adjudication system employed by a healthcare provider evaluates electronic claim data before it is submitted to a payer institution. Healthcare providers do their best to ensure claims are accurate before they send them to the payer by embedding payer rules into their software applications or by utilizing "claim scrubbing" applications to evaluate claim data prior to submission to the payer. Known systems also approach claim data processing from a piecemeal perspective whereby, for example, one software vendor system addresses online eligibility and electronic remittance and a different vendor system addresses revenue management from a physician perspective. Another vendor system supports claim editing, but only after the claim is generated. Further known systems require significant user intervention once a claim is produced. Known systems fail to approach claims processing and management from a combined payer, provider and patient perspective. Another problem with known processes is that rules used by a healthcare provider may be inaccurate, obsolete, or comprise an incorrect version or may otherwise be different to those in current use by a target payer institution. Further, known systems typically do not address compatibility of healthcare provider and payer systems. This results in claims that fail the edit process upon receipt by the payer and consequent disallowance by the payer. Disallowed claims cause delayed payment and negatively impact healthcare provider cash flow and patient satisfaction with the process. A system according to invention principles improves claim accuracy prior to claim submission to a healthcare payer institution.

SUMMARY OF INVENTION

A claim pre-processing system employs trial adjudication to improve claim accuracy prior to claim submission to a healthcare payer institution or other entity. A system processes claim data related to provision of healthcare to a patient The system includes a claim data collator for collating data related to a claim for a particular patient for submission to a payer and a source of rules for use in processing collated claim data. A pre-processor submits the collated claim data for processing using the rules to validate the collated claim data is in condition for processing to initiate generation of payment. A claim processor submits the collated claim data to a payer, in response to successful validation by the pre-processor.

In a feature of the invention the system includes a rules processor for processing acquired claim data to identify a condition triggering application of a different set of rules for determining validity of an individual claim element.

In another invention feature the pre-processor re-submits amended collated claim data for processing using the rules to validate the collated claim data is in condition for processing to initiate generation of payment, the amended collated claim data being received in response to unsuccessful validation using the rules.

BRIEF DESCRIPTION OF THE DRAWING

FIG. 4 shows a user interface display image illustrating a patient claim billing record for multiple patient encounters with a healthcare provider concerning treatment of an injury, according to invention principles.

FIG. 5 shows a user interface display image illustrating a record for a particular patient claim, according to invention principles.

FIG. 6 shows a user interface display image illustrating claim pre-processing results and identifying claim rejection reasons by description and rejection code, according to invention principles.

FIG. 7 shows exemplary rules and associated error code results of applying rules to patient claim data, according to invention principles.

FIGS. 8-14 show data records including data elements incorporated in a central data repository used in claim processing, according to invention principles.

DETAILED DESCRIPTION OF INVENTION

Figure 1:
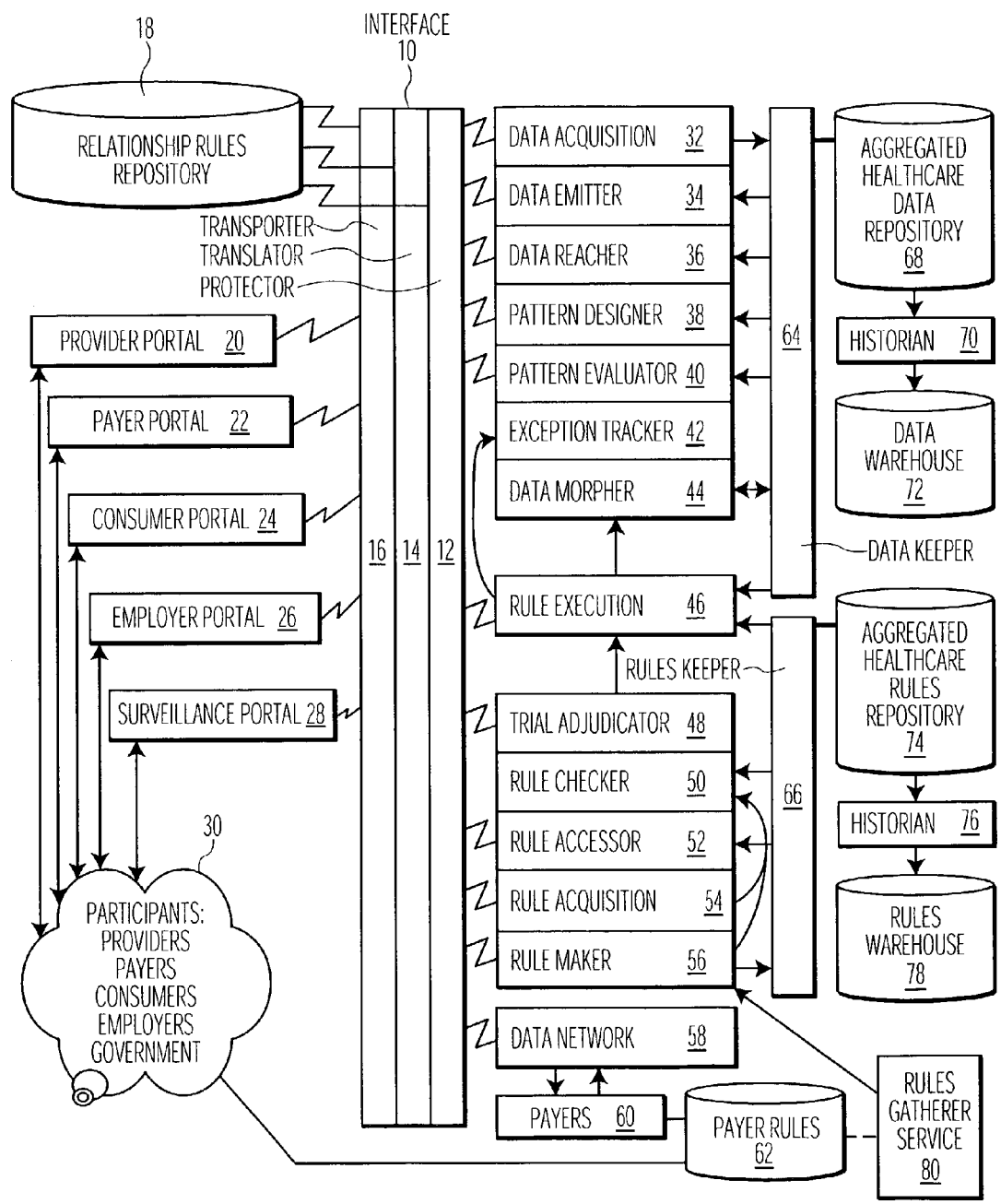
FIG. 1 shows an overall claim processing system employing trial adjudication to improve claim accuracy prior to claim submission to a healthcare payer institution or other entity, according to invention principles.

FIG. 1 shows an overall claim processing system employing trial adjudication to improve claim accuracy prior to claim submission to a healthcare payer institution or other entity. In the FIG. 1 system, continuously updated centralized common rules in repository 74 are employed to ensure that individual healthcare providers, as well as individual healthcare payer institutions are working with the most up-to-date version of the rules. Use of centralized rules ensures that a healthcare provider is able to comply with the latest provisions of the rules. A rule as used herein comprises a procedure for determining that healthcare claim elements comply with predetermined requirements including, health plan reimbursement conditions, health plan format requirements, a reimbursement formula, reimbursement constraints and a reimbursement computation procedure. A rule also may comprise a prescribed guide, a precept, or a model for how to present, conduct or regulate an action by using a form and data or the relations between form and data. Further, an exception as used herein encompasses the identification of an issue and mechanism to process that issue.

The FIG. 1 system automates the pre-registration, eligibility, registration authorization, claim generation, trial adjudication, claim submission, payment remittance, and post-remittance processes of a health care claim data processing cycle to provide seamless, accurate and prompt processing. The system automates coordination of employer and payer activities and ensures that pre-visit enrollee data is accurate. Thereby, if a patient uses a consumer portal (24) to schedule a visit or if a healthcare facility collects insurance information from a patient, medical necessity, referral and eligibility verification processing is automatically initiated. A claim is evaluated for accuracy and edited by a rule execution function 46 and adjudication unit 48, using the applicable rules in rules repository 74, both before the claim is completed (i.e. as individual claim elements for individual healthcare encounters post to the claim, for example) and again before the completed claim is submitted for payment. A variety of portals 20-28 in the FIG. 1 system are controlled and administered by interface 10 to provide claim data access to patients, payers, providers, employers and government agencies. The system facilitates healthcare provider compliance with governmental and payer rules through use of automated, rules-based editing and review systems.

The FIG. 1 system automatically edits claim data to ensure claims are error free. The system advantageously performs claim trial adjudication (pre-processing) using the rules to validate that edited collated claim data is in condition for submission for actual adjudication by a payer institution to initiate generation of payment. Thereby incidence of partial or complete claim rejection is reduced which correspondingly reduces operational costs for both the providers and payers. Payers are enabled to efficiently increase the daily volume of claims processed, since claims are accurate and electronically received. This also reduces the volume of inquiry phone calls from providers and patients concerning insurance coverage and claim matters. Providers benefit through a shortened revenue cycle resulting in quicker remittance payments, reduced staff intervention and improved patient satisfaction. A failure in trial adjudication automatically initiates deficiency correction or manual intervention via scheduling of a worklist task to be performed by expert personnel. Upon successful trial adjudication, the claim data is automatically re-queued for electronic submission to the payer. Payment advice is processed electronically without manual intervention and automatically posted to the appropriate account.

The FIG. 1 system comprises functions implemented in software applications and executable procedures for processing claim data. These functions may also be implemented in hardware or a combination of both hardware and software resident in one or more computer systems and servers and involving one or more communication networks for internal and external communication. The system processes claim data related to provision of healthcare to a patient by collating data related to a claim for a particular patient for submission to a payer. The collated claim data is submitted for pre-processing using rules to validate the collated claim data is in condition for processing to initiate generation of payment. Upon successful validation the validated claim data is submitted to a payer. The claim data is collated by data acquisition unit 32 via interface 10 for storage in data repository 68. Repository 68 contains financial and clinical data related to healthcare encounters that are currently ongoing. Data acquisition unit 32 is able to receive both solicited and unsolicited data from multiple different sources and to request data from these sources via interface 10. The different sources include external users (participants) subscribing to and using the FIG. 1 system and may include for example, healthcare providers, healthcare payer institutions (e.g. insurance companies, Health Maintenance Organizations—HMOs etc.), consumers, employers, and government agencies.

Data keeper unit 64 acts as a gateway and data management system governing data storage and retrieval for healthcare data repository 68 and processing requests to use repository 68 to store, modify, and retrieve data. Data keeper unit 64 also tracks data changes in repository 68 by recording time, date and nature of changes made as well as the source and identity of the author of the changes to maintain a data update audit trial. Historian unit 70 is used in archiving and maintaining older data value versions and is specifically used in archiving data records associated with patient encounters following completion of financial transactions (i.e. encounters for which no related financial transactions are outstanding) and processing for these encounters. An encounter as used herein comprises a patient encounter with a healthcare enterprise involving patient and healthcare enterprise interaction that has a financial or transaction consequence and may include for example a patient visit, phone call, inpatient stay or out-patient treatment etc. Records of such encounters are maintained by data keeper unit 64 in repository 68. Historian unit 70 stores archived data in archive (data warehouse) database 72.

The collated claim data is submitted for pre-processing by trial adjudicator 48 using rules to validate the collated claim data is in condition for processing to initiate generation of payment. Trial adjudicator 48 initiates execution of a sub-set of rules executed by rule execution unit 46. Unit 46 detects the occurrence of an event triggering application of associated rules and executes the rules associated with that event. An event may include receipt of data to add to the repository 68, a request to execute a specified list of rules, and an event triggered by the activities of a function within the FIG. 1 system. A rule executed by unit 46 may itself generate a triggering event and initiate execution of other rules. An individual rule may contain a test resulting in assignment of a result status of "True" or "False" upon execution of a rule. An individual rule may also contain lists of actions to be performed upon a true result and alternate actions to perform upon a false result, for example. The list of actions may include, creation of worklists of tasks for automatic or manual performance, creation of logs and audit reports and accounting reports, creation of error reports, generation of claims, posting of remittances, modification of data, and other actions. Data Morpher unit 44 comprises a sub-category of actions that rules invoke to modify data in repository 68 in response to command. Unit 46 also processes and executes rules stored in the Relationship Rules Repository 18 that contains rules required and used by the Protector 12, Translator 14, and Transporter 16 during communication involving interface 10.

The rules executed by trial adjudication unit 48 determine expected adjudication results when a specified set of claim data is submitted to a specified payer. Unit 48 uses rules derived from repository 74 (or from rule accessor 52) via rule keeper interface 66 to predict the result of submitting a specified set of claim data to a specified payer. For this purpose the rules used by unit 48 replicate the rules used by the selected specific payer. Unit 48 identifies conditions that would lead to denial of payment and enables such conditions to be fixed (automatically or with manual intervention) before a claim is submitted to a designated payer. This procedure advantageously facilitates the creation of error-free claims using rules derived from repository 74 or using remotely accessed rules. Rules including regulatory guidelines and directives are continuously acquired for storage in repository 74 and are continuously updated and maintained in this repository via rules keeper unit 66. Rules archiving unit 76 in conjunction with unit 66, dates and time stamps rules to be archived and stores obsolete, expired or older version rules in archive (rules warehouse) database 78. Archived rules are accessible and usable to determine an outcome based on submission of particular claim data for adjudication using rules in force at a date in the past, for example. Repository 74 contains adjudication rules acquired from payer institution participants and rules that are established from previous transactions with payers. Repository 74 also contains rules developed by the system and by authorized participants that add automated processes to the system. Pattern designer unit 38 creates specialized rules that define surveillance research processes and rule maker unit 56 is used to create general purpose rules.

Unit 48 uses rules in repository 74 derived from external rule sources (such as rules 62 owned by a payer institution 60) by rule accessor 52 via interface 10 and data network 58. Network 58 may comprise a conventional network such as LAN (local area network), WAN (wide area network) or the Internet or alternatively may comprise a network service such as a clearinghouse or other service used by a healthcare payer or a healthcare provider to facilitate data and rule (e.g., payer rules 62) acquisition for claim adjudication. Payer rules 62 are rules promulgated by a payer 60 that are not accessible through the automated process managed by Rule acquisition unit 54. Rather rules 62 are manually determined through manual acquisition processes and are parsed and analyzed by Rule acquisition unit 54 by using a user interface provided by rule maker unit 56. The Rule Maker 56 user interface supports manual creation, review and update of rules including those acquired via unit 54. Unit 56 also prompts a user with lists of available tests and actions and guides the user through the process of constructing and editing rules prior to storing the edited rules in Rules Repository 74.

Rule acquisition unit 54 accumulates rule data by automatic interrogation of payers systems for rules and through documentation and other information provided by payers that do provide access to their proprietary programmed rule sets. Unit 54 retrieves payer generated information bulletins from payer websites and other sources and analyzes this material to identify information representing new or changed rules for incorporation in repository 74 and to identify rules that have expired. Further, individual payer institutions may use Payer Portal 22 to communicate rule information via interface 10 to acquisition unit 54 which incorporates them using rule keeper unit 66 in repository 74. Unit 54 also receives new rules following user manual data entry and processing via a user interface provided by rule maker 56 based on information acquired from payers by rules gatherer service 80. Payers forward updated rule information to service 80 in advance of implementing a new rule or rule version, for example. Service 80 supports user creation of implementable definitions of these new or updated rules using Rule Maker user interface 56 for incorporation in rules repository 74. Service 80 also monitors claim rejection issues and rates of adjudication success and failure and supports adjustment or creation of rules to resolve identified issues. Rule Checker unit 50 monitors rules in repository 74 and identifies and indicates to a user those rules that are incomplete or contain incorrect syntax. Unit 50 also reports combinations of rules that are mutually inconsistent. Further, in response to identification of a predetermined exception condition during claim data processing by rule execution unit 46 and trial adjudication unit 48, exception tracker function 42 employs a sub-set of rules managing the processing and reporting of an identified exception condition. Exception tracker function 42 may be invoked by rule execution unit 46 in response to execution of a particular rule or upon a particular result of executing a rule. Upon determination of an exception condition, function 42 may schedule manual intervention, via a user interface or a worklist or by communicating a report or message to a recipient, for example.

Trial adjudicator 48 uses rule accessor 52 to submit claim data for trial adjudication by remotely located rules. These remotely located rules may be maintained (and owned) by a different entity (such as a payer institution) to the owner of the FIG. 1 system. A payer who owns such rules establishes a procedure for receiving claim data for trial adjudication and responds with a report indicating how the submitted claim data would be adjudicated using the payer owned rules.

Claim data used for trial adjudication and ultimately submitted to a payer upon amendment (if required) and validation is derived from data repository 68. FIGS. 8-14 show an exemplary data record structure for data elements incorporated in central data repository 68 and used in claim processing. Specifically, FIG. 8 shows a partial patient record data structure, FIG. 9 shows a medical record data structure and FIG. 10 shows a partial payer record data structure. A charge record data structure and occurrence code data structure are presented in FIGS. 11 and 12 respectively and FIGS. 13 and 14 indicate a span code (for use in identifying service charges that are to be grouped on a single claim) and a medical condition code data structure respectively. These record structures are exemplary only and repository 68 typically contains other types of records associated with claim data such as, for example, records concerning ambulance services, rehabilitation services, treatments and other services and activities. The record structures of FIGS. 8-14 are individually accessible in repository 68 using a claim packet identifier (800, 900, 920, 940, 960, 980, 830), section identifier (802, 902, 922, 942, 962, 982, 832) and sequence number (804, 904, 924, 944, 964, 984, 834).

Data in an individual record data structure is field length delimited. In the patient record structure of FIG. 8, for example, a patient last name (806) occupies a fixed length of 20 characters, followed by a patient first name (808) occupying twelve characters and middle initial (810) occupying one character. The record structures of FIGS. 9-14 contain data related to other particular claim data aspects in similar predetermined fixed length fields. The medical record of FIG. 9, for example, contains an admission diagnosis code (906), as well as a primary diagnosis code (908) and other diagnosis codes (910). The payer record of FIG. 10 contains a source of payment code (926), as well as payer identifier (928) and payer sub-identifier (930). The charge record of FIG. 11 contains a service charge code (946), as well as a service charge revision code (948) and service date (950). The occurrence code record of FIG. 12 contains an occurrence identification code (966) and occurrence date (968). The span code record of FIG. 13 contains a span identification code (986), as well as a span determination start date (988) and end date (990) for use in identifying codes and the related dates that identify an event that relates to the payment of this claim. The condition code record of FIG. 14 contains a medical condition identification code (836). The items referred to in connection with FIGS. 8-14 are described for exemplary purposes. However, other record items are shown in the record structures of FIGS. 8-11. These other items are representative of the breadth of data that may be included in the various records in the repository 68 structure, for example. In an alternative embodiment, other non-fixed length data record structure or another data record structure may be employed for repository 68.

The claim data in repository 68 is collated by data acquisition unit 32 via interface 10 from multiple different sources as previously described and stored in repository 68 via data management system 64. A data emitter unit 34 provides claim data to an external entity (e.g., portals and participants 20-30) by extracting required claim data from repository 68 and communicating it via interface 10. Data reacher unit 36 is used by functions of the FIG. 1 system to provide read-only access to claim data stored by a remote entity and to make decisions based on this data. Further, claim data repository 68 is searchable by users 30 via external portals 20-28 using data search criteria created using search pattern design function 38. Thereby a user may search for statistically significant data patterns and other data patterns in analyzing the claim data in repository 68.

Search design function 38 employs a specialized category of rules stored in rules repository 74. An authorized user is able to use surveillance portal 28 via interface 10 to use the specialized category of search rules to support a search of rules and claim data information. Searchable information sources include rules repository 74, relationship rules repository 18 as well as claim data repository 68. For this purpose, search pattern evaluator function 40, employs a sub-set of rules executed by rule execution unit 46 to process a definition of a pattern search created by pattern design function 38. Specifically, pattern evaluator function 40 identifies patterns in the data searched according to action steps included in the search definition and reports results to the search initiator via interface 10. A pattern search is executable in response to occurrence of an event. An event may include, for example, a command (in response to a request by a participant), or upon detection of a change in particular data (receipt of a specific diagnosis, for example) or an event may be internally generated such as in response to expiration of a particular time period.

Interface 10 provides access by various interested participants 30 in the claim data processing operation via portals 20-28 for searching, viewing or initiating actions. Thereby a participant (such as a healthcare provider, payer institution representative, patient, employer or government agency) is able to access claim data, payer rules and initiate various actions such as a data correction action, for example. Specifically healthcare providers and healthcare payer representatives are able to access the system via portals 20 and 22 that provide the functions these entities respectively require. A healthcare provider, for example, is able to input financial data and associated clinical data into repository 68 and to initiate and manage claim trial adjudication and other rule-driven processes via portal 20. Similarly, a provider is able to automatically modify its own data based on automated rules or through manual amendment and update. A provider is further able to initiate submission of validated error-free claims for payment and to initiate claim status inquiries. In addition, a provider via portal 20 is able to acquire remittance advice (i.e., information about payments made) and to automatically post acquired advice to corresponding correct accounts as well as to generate and submit secondary and tertiary claims and obtain worklists (of tasks to be performed) and reports in support of management of its business.

A payer institution is able to use portal 22 to store and maintain adjudication rules in repository 74 and to receive claim data for trial or actual (determinative) adjudication as well as to respond to claim status inquiries. A payer is further able to communicate a request for information or issue remittance advice and obtain worklists and reports and manage its business and revenue cycle. A consumer, such as an individual patient, covered dependent or healthcare plan subscriber with appropriate authorization is able to use consumer portal 24 to view his own claim data records and claim status and research rules governing payment. A consumer is also able to correct errors in his own demographic data or medical record and to schedule appointments via the system. A consumer is also able to obtain account balance, recent transaction records, future deposit information and request payment from a medical expense reimbursement account for items paid out of pocket.

An employer, or another plan administrator, is able to use portal 26 to manage healthcare encounter cycle business and to negotiate healthcare contracts on behalf of a group of persons (employees) and to monitor activity related to those employees. For this purpose, an employer is able to obtain, for example, a worklist or a report identifying incidence of various diagnoses, utilization of various providers, a breakdown of charges (e.g. those paid by members, contractually reduced, or denied). Thereby an employer is able to determine if plan members would benefit from an alternative health plan selection. Surveillance portal 28 enables authorized participants 30 (e.g. a regulator or researcher) to create and implement research projects to analyze stored claim data by searching for patterns or trends in the claim data of repository 68 in conjunction with rules repository 74. Specifically, surveillance portal 28 in conjunction with search pattern design and implementation units 38 and 40 respectively, supports searches to, (1) generate periodic statistical reports, (2) detect claim fraud and abuse, and (3) detect outbreaks of epidemics, caused either by natural disease or by human (terrorist) activity and other searches, for example. Search results may include worklists or reports and search criteria may be stored as rules in rules repository 74.

Interface 10 provides access by participants 30 to claim data and rule repositories 68 and 74 via portals 20-28 using a security function 12, translator function 14 and transport function 16. Security function 12 determines whether a participant is authorized to communicate with another particular participant and whether a participant is authorized to access particular data and assigns participant privileges and entitlements and maintains security and access rules. Unit 12 rejects and tracks unauthorized requests that violate security and other (e.g., HIPAA) policies. Translator function 14 converts data between the different data formats used by internal and external participants in the FIG. 1 system. For this purpose, translator 14 converts data from a first data format into an internally defined intermediate data format and from the intermediate format into a desired output data format. Transport function 16 supports communication of data and messages between internal functions of the FIG. 1 system and between internal functions and external participants. For this purpose function 16 uses relationship rules repository 18 to identify required connection protocols and methods as well as source and destination addresses. Function 16 also uses rules repository 18 in encoding data in the appropriate message format and protocol and in initiating necessary hand shaking and other routines required to implement bidirectional communication.

Relationship rules repository 18 contains information identifying the application programmer interfaces (APIs) used by participant and system software applications and the required procedure for requesting information from particular sources and providing information to particular participants. The participant API identification and related communication information is provided by individual participants for storage in repository 18. The participants retain control over and maintain their respective communication support information. Interface 10 uses the stored predetermined API and communication information in supporting conversion of data from a first data format into an internally defined intermediate data format and from the intermediate format into a desired output data format. As a consequence, participants are able to update their own systems and to communicate with other participants regardless of the rule standards in use or whether the repositories are migrated to new platforms or radically altered in other ways. Also data format standards involved may be changed by an individual participant without impeding operation by other participants.

Figure 2:
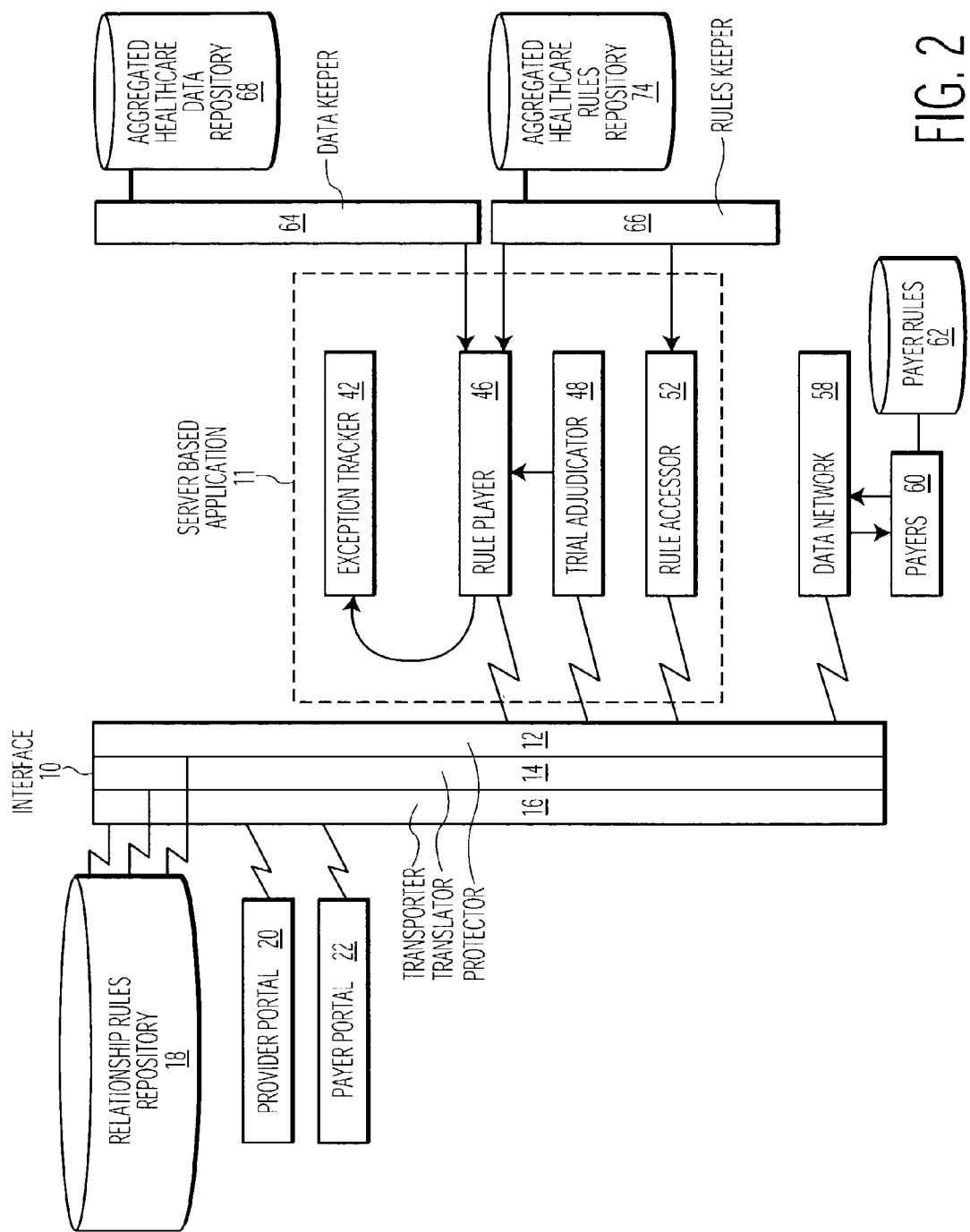
FIG. 2 shows a trial adjudication system used in the overall claim processing system of FIG. 1, according to invention principles.

FIG. 2 shows a trial adjudication system including server based functions (specifically functions 42, 46, 48 and 52 in server application 11) used in the overall claim processing system of FIG. 1. As previously described, collated claim data derived from repository 68 via unit 64 is submitted for preprocessing by trial adjudicator 48 in conjunction with rule execution unit 46 using rules derived from repository 74 via unit 66. Thereby the trial adjudication system determines expected adjudication results when a specified set of claim data is submitted to a specified payer and validates the collated claim data is in condition for processing to initiate generation of payment. The result of the trial adjudication is accessible by a provider or payer using portals 20 and 22 respectively via interface 10 directed by management rules in repository 18. A particular rule result that gives rise to an exception condition invokes operation of exception processing 42 to schedule manual intervention, via a user interface or a worklist or by communicating a message to a recipient, for example. Further, unit 48 uses rules in repository 74 which may include rules derived from external rule sources (such as rules 62 owned by a payer institution 60) by rule accessor 52 via interface 10 and data network 58, for example.

Figure 3:
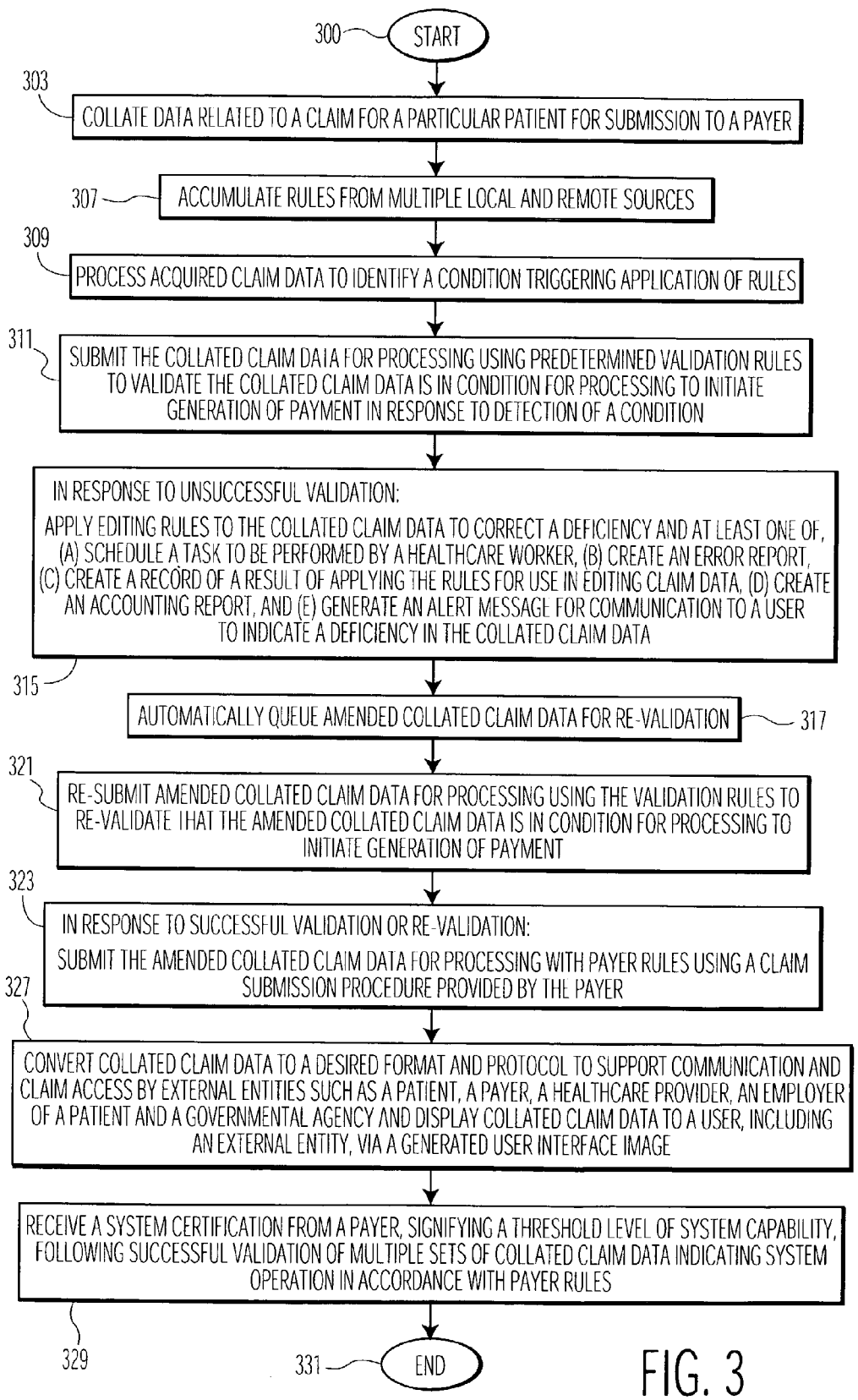
FIG. 3 shows a flowchart of a process employed in claim processing by the systems of FIGS. 1 and 2, according to invention principles.
Figure 5:
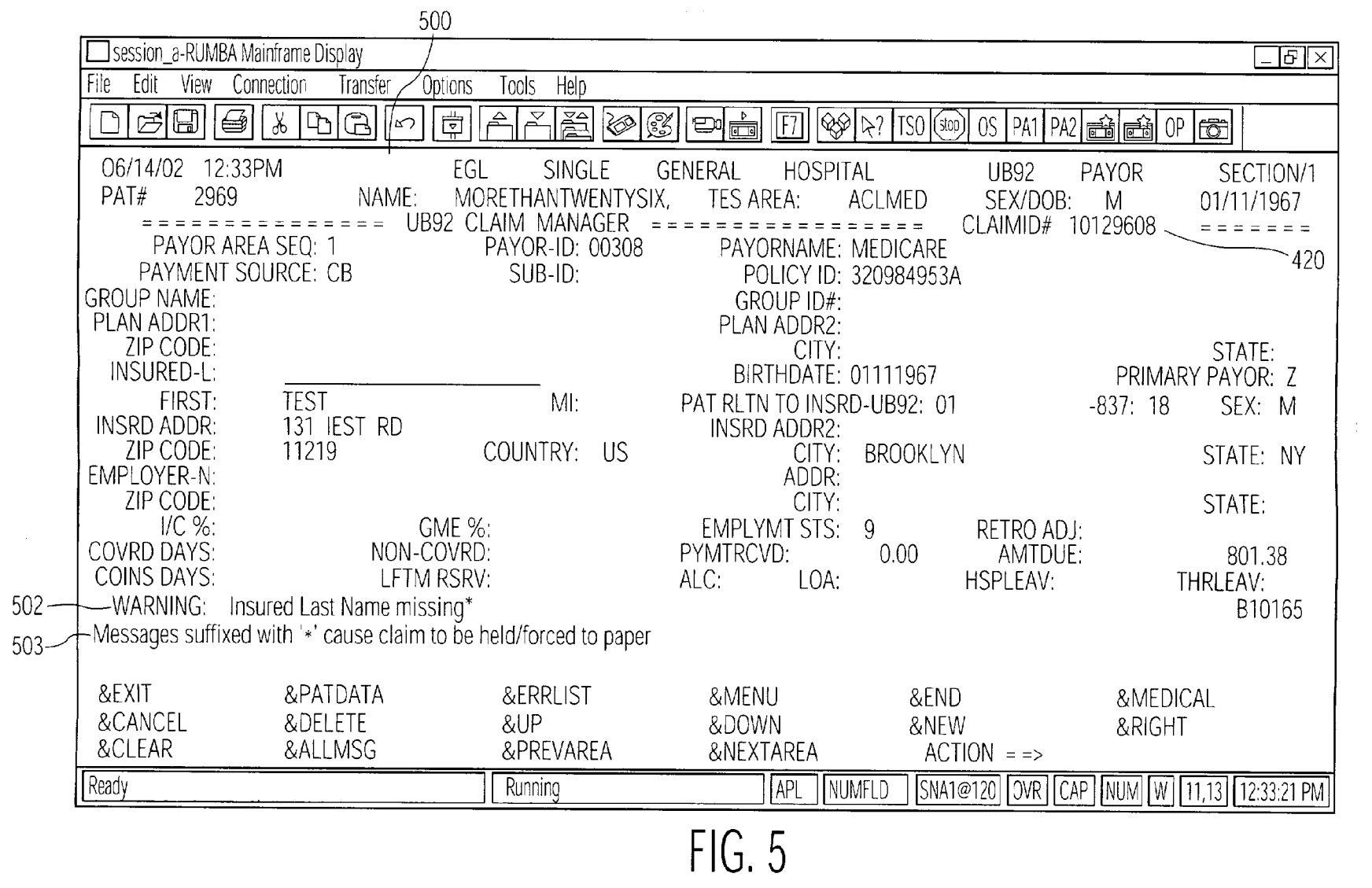

FIG. 3 shows a flowchart of a process employed by the system of FIG. 1 in claim processing. In step 303 acquisition unit 32 in conjunction with data interface unit 64 collates data related to a claim of a particular patient for storage in data repository 68. FIG. 4 shows a user interface display image illustrating a claim billing record for a particular patient (the patient is identified by item 420). The billing record includes collated claim data for multiple patient encounters 402, 404 and 406 with a healthcare provider concerning treatment of an injury. FIG. 5 shows a user interface display image 500 illustrating another format record for the same particular patient (item 420) indicating payer related information. In step 307, rules acquisition unit 54 (and 52) accumulates rules for storage via interface unit 66 in repository 74. The rules are accumulated from local and remote sources including, payer institutions, messages received from payer institutions, payer institution websites, a rule creation processor used to create rules in response to previously identified claim data deficiencies and regulatory guidelines and directives from governmental and regulatory rule providers. In step 309, trial adjudication processor 48, in conjunction with rule execution unit 46 processes collated claim data acquired from repository 68 to identify a condition triggering application of a first set of rules used for determining validity of an individual claim element of the collated claim data. Units 46 and 48 apply a first set of rules in response to detection of a first condition state and a second set of rules in response to detection of a second condition state (both sets of rules being derived from repository 74). A condition triggering application of rules may include, for example, (a) generation of a record for incorporation in claim data for a patient, (b) detection of a record addition to claim data for a patient, (c) detection of a record addition to a patient billing record, (d) detection of a change in a patient billing record and (e) detection of a change in claim data for a patient.

An individual validation rule may contain one or more tests to identify a true condition and initiate an associated first set of actions or a false condition and initiate an associated second set of actions. A rule may detect the absence of an insured persons name as illustrated in the warning item 502 in the claim record of FIG. 5, for example. Item 503 further indicates this warning condition triggers holding of the claim and generation of a report. A rule test condition may be simple or complex involving a combination of tests linked with logical operators (e.g., "and," "or," "not"). Individual linked tests results are logically combined to provide an overall test true or false result. Further, a set of actions may be an empty set triggering no actions. If no trigger condition is detected a default true condition is declared. Rules repository 74 (FIG. 1) includes executable rules and the test components incorporated within the individual rules together with an English language description documenting individual rule function for use in help prompts and explanation to nontechnical users and other users. A start and end date and time indicating a period of validity is also maintained by repository 74 for both a rule and individual test components incorporated by the individual rule. Unit 46 examines rule validity periods and does not execute a rule or test component at a time and date falling outside of a period of validity.

In step 311 (FIG. 3), trial adjudication unit 48 submits the collated claim data for processing by unit 46 (FIG. 1) using a set of rules identified in step 309 (e.g., a first set of claim data validation rules) to validate the collated claim data is in condition for processing to initiate generation of payment. If a remotely located set of rules is identified in step 309 (e.g., rules maintained by a payer institution), unit 48 submits the collated claim data for processing with the remotely located rules using a claim data submission procedure (stored in repository 74) provided by the rule owning institution. For this purpose unit 48 employs rule accessor 52 and network 58 in accessing the remotely located rules 62 via payer institution 60, for example. An individual validation rule comprises a procedure for determining claim elements comply with predetermined requirements such as, health plan reimbursement conditions, health plan claim format requirements, a reimbursement formula, reimbursement constraints or a reimbursement computation procedure, for example. An exemplary rule detects inconsistency between data fields such as data fields retaining a telephone number, zip code, address or other geographical identifier of the collated claim data. Alternatively, a rule may determine whether an element of the collated claim data exceeds a payer designated limit, for example. Further, an individual claim element processed by a rule may comprise, a portion of a claim, a complete claim, individual records of a claim or record data associated with an individual patient encounter with a healthcare service provider, for example.

FIG. 7 shows exemplary rules and associated corresponding error codes (in the left column) identifying any errors resulting from application of the rules to patient claim data. The rules are categorized and comprise a first set of rules (rules 703-707 in category 2 in FIG. 7 right column) for determining validity of an individual claim element and a second set of rules (rules 700, 709, 717-721 in category 1 in FIG. 7 right column) for use in processing collated claim data for a completed claim. Some rules (rules 711-715) reside in both categories. Rules 703 and 705, detect and generate a warning if a date of a service provided to a patient conflicts with prescribed reimbursement date ranges and rule 707 detects and generates a warning if a particular procedure code is not covered by a particular payer plan, for example. Similarly, rule 709 identifies and generates a warning for an invalid patient admission date and rule 717 identifies and generates a warning if an occurrence (e.g., an injury) date falls after an admission date. Rules 711, 713 and 715 detect and generate a warning if a diagnosis code, procedure code or a combined code of a service provided to a patient, conflicts with the recorded age or gender of the patient concerned. Rule 700 detects and generates a warning if a claim contains a cause of injury but no place of injury. Rule 719 detects and warns of invalid inpatient revenue codes and rule 721 detects and warns of improperly combined charges in this case mammogram charges are to be separately billed, for example. Unit 48 (FIG. 1) in conjunction with unit 46 automatically corrects deficiencies identified by the rules in repository 74 (e.g., the rules of FIG. 7) using claim data information in repository 68 to resolve inconsistencies or to add missing data. If a condition is detected that is not automatically resolvable human intervention and review is scheduled as previously described.

FIG. 6 shows a user interface display image illustrating claim pre-processing results of applying validation rules in step 311 (FIG. 3) and identifying claim rejection reasons by description and rejection code. Specifically, line 600 indicates error list heading labels defining columns comprising, an error code sequence, an error code identifier and level, an error code sub-identifier, error description text and cleared errors identifying errors that have been corrected (none in this example). Lines 602-617 list results of applying validation rules in step 311 to claim data for a patient. The results list identifies 7 claim rejection reasons comprising, an invalid revenue code (602), a data format deficiency (607), a missing name portion (609), an accommodation data omission (611), a revenue code related error (613), a procedure code related error (615) and accommodation or ancillary data omission (617).

In step 315 of FIG. 3, in response to unsuccessful claim validation in step 311, trial adjudication unit 48 in conjunction with unit 46, applies rules for use in editing the collated claim data. Specifically, units 48 and 46 automatically edit the collated claim data to correct an identified deficiency likely to result in claim denial. Units 48 and 46 also initiate functions involving manual data review or manual intervention in the claim data correction process. Such functions include, for example, scheduling a task to be performed by a healthcare worker (such as to correct a deficiency in the collated claim data), creating an error report for review, creating a record of a result of applying the claim data editing rules (for use in future claim data editing), generating an alert message to a user to indicate that a deficiency in the collated claim data is likely to result in claim denial, creating an accounting report, generating a claim and initiating sending of a remittance. Other functions include, initiating pattern searches and other statistical analyses of claim and other data, maintaining logs of activities, adding items to reports, and categorizing sets of data (to indicate for instance, one claim is error-free, but that another claim is on a particular worklist for correction). In step 317, following automatic or manual editing of the collated claim data to provide amended claim data, unit 48 automatically queues the amended collated claim data for re-validation by unit 48 in conjunction with unit 46.

In step 321, trial adjudication unit 48 in conjunction with unit 46, re-submits the claim data (amended in step 315) for processing using the validation rules. This is done to re-validate whether the amended claim data is in condition for processing to initiate generation of payment. In response to successful claim data re-validation in step 321 or successful validation in step 311, unit 48 employs interface 10 and network 58 in step 323 to submit the validated claim data to a payer to initiate payment. For this purpose interface 10 uses relationship repository 18 to process the validated claim data to provide the data format, protocol, handshaking routine and submission procedure predetermined (and retained and identified in repository 18) by the payer. In response to receiving the validated claim data, a payer accepts and adjudicates the validated claim data and records issuance of a remittance to the claimant healthcare provider and patient (if applicable). A healthcare provider also generates an additional secondary claim to a secondary provider in the case that a claim is partially covered by a primary payer and another claim portion is covered by a secondary payer. The secondary claim trial adjudication and submission procedure similarly follows the process of FIG. 3 for a primary claim.

In response to an unsuccessful re-validation in step 321, unit 48 initiates scheduling of manual review of the claim data. In an alternative embodiment, the FIG. 3 process may be repeated starting at step 315 for a predetermined number of iterations prior to declaring failure and initiating manual claim review. Upon completion of processing of validated claim data, the claim data is archived in data warehouse 72 via historian unit 70. In step 327, unit 48 employs interface 10 to support claim data access and exchange of data between the system and external entities such as a patient, a payer, a healthcare provider, an employer of a patient and a governmental agency. The accessed data is displayed to a user via a generated user interface image on portals 20-28, for example. For this purpose interface 10 uses relationship repository 18 to process the accessed claim data to provide the claim data in the predetermined data format and communication protocol desired by the requesting external or internal entity. Similarly, interface 10 uses relationship repository 18 to process the accessed claim data to implement the predetermined handshaking routine and submission procedure desired by the requesting entity.

In step 329, following successful validation of multiple sets of collated claim data verifying the system operates in accordance with particular payer rules, a system certification is obtained from the particular payer. This certification signifies a threshold level of capability of the FIG. 1 system has been achieved. The process detailed in the flowchart of FIG. 3 ends at step 331.

The systems, processes and user interface display formats presented in FIGS. 1-14 are not exclusive. Other systems, processes and user interface forms may be derived in accordance with the principles of the invention to accomplish the same objectives. The inventive principles are applicable to streamlining and automating a revenue management process in any industry or field. The principles are particularly applicable to the insurance, government and healthcare industries.

What is claimed is:

1. A system for processing claim data related to provision of healthcare to a patient, comprising:
   a claim data collator for collating data related to a claim for a particular patient for submission to a payer;
   a source of rules for use in processing collated claim data;
   a pre-processor for submitting said collated claim data for automatic trial adjudication by a healthcare provider to determine expected adjudication results including expected reimbursement prior to submission for adjudication by a payer using said rules to validate said collated claim data is in condition for processing to initiate generation of payment;
   a claim processor, for submitting said collated claim data to said payer for adjudication by said payer, in response to successful validation by said pre-processor; and
   a rule creation processor for automatically creating said rules for use in processing collated claim data in response to previously identified claim data deficiencies wherein
   said pre-processor re-submits amended collated claim data for processing using said rules to validate said collated claim data is in condition for processing to initiate generation of payment, said amended collated claim data being received in response to unsuccessful validation using said rules.

2. A system according to claim 1, wherein
   a rule comprises a procedure for determining claim elements comply with predetermined requirements including at least one of, (a) health plan reimbursement conditions, (b) health plan claim format requirements, (c) a reimbursement formula, (d) reimbursement constraints and (e) reimbursement computation procedure.

3. A system according to claim 2, wherein
   said claim elements comprise at least one of, (i) a portion of a claim, (ii) a complete claim, (iii) individual records of a claim and (iv) record data associated with an individual patient encounter with a healthcare service provider.

4. A system according to claim 1, wherein
   a rule at least one of, (a) detects inconsistency between a plurality of data fields of said collated claim data and (b) determines whether an element of said collated claim data exceeds a payer designated limit.

5. A system according to claim 4, wherein
   said plurality of data fields includes two or more of, (i) telephone number, (ii) zip code, (iii) address, (iv) another geographical identifier, (vi) clinical data and (vii) other claim data.

6. A system according to claim 1, wherein
   said pre-processor automatically queues amended collated claim data for re-validation by said pre-processor.

7. A system according to claim 1, wherein
   said pre-processor initiates generation of an alert message to a user to indicate a deficiency in said collated claim data likely to result in claim denial, in response to unsuccessful validation by said pre-processor, said deficiency being identified as a result of said validation.

8. A system according to claim 1, wherein
   said pre-processor initiates scheduling of a task to be performed by a healthcare worker in response to unsuccessful validation by said pre-processor, said task comprising correcting a deficiency in said collated claim data likely to result in claim denial.

9. A system according to claim 1, wherein
   said pre-processor processes said collated claim data to correct a deficiency in said collated claim data likely to result in claim denial, in response to unsuccessful validation by said pre-processor.

10. A system according to claim 1, wherein
    said source of rules is at least one of, (a) a remotely located rules source provided by a payer, and (b) a rule repository and
    said pre-processor submits said collated claim data for processing with said payer rules using a claim submission procedure provided by said payer.

11. A system according to claim 1, including
    a rules accumulator for accumulating rules, to be retained by said source of rules, from at least one of a plurality of sources including, (a) a payer, (b) payer messages, (c) payer websites, (d) a rule creation processor for creating rules in response to previously identified claim data deficiencies and (e) regulatory guidelines.

12. A system according to claim 1, including
    a rules processor for processing acquired claim data to identify a condition triggering application of rules.

13. A system according to claim 12, wherein
    said rules processor, in response to an identified condition, applies rules for use in editing claim data.

14. A system according to claim 13, wherein
    said rules processor applies a first set of rules in response to a first condition state and a second set of rules in response to a second condition state.

15. A system according to claim 12, wherein
    said rules processor processes acquired claim data in response to an event including at least one of, (a) generation of a record for incorporation in claim data for a patient, (b) detection of a record addition to claim data for a patient, (c) detection of a record addition to a patient billing record, (d) detection of a change in a patient billing record and (e) detection of a change in claim data for a patient.

16. A system according to claim 12, wherein
    said rules processor, in response to application of said rules for use in editing claim data performs at least one of, (a) schedules a task to be performed by a healthcare worker, (b) creates an error report, (c) creates a record of a result of applying said rules for use in editing claim data, (d) creates an accounting report, (e) generates a claim and (f) accepts a remittance.

17. A system according to claim 12, wherein
    said rules processor, in response to identification of a condition, initiates scheduling of review of acquired claim data to be performed by a healthcare worker.

18. A system according to claim 1, including
    a user interface supporting access to collated claim data by at least one of, (a) a patient, (b) a payer, (c) a healthcare provider, (d) an employer of a patient and (e) a governmental agency.

19. A system according to claim 1, including
    an interface processor supporting exchange of data between said system and external entities including at least one of, (a) a patient, (b) a payer, (c) a healthcare provider, (d) an employer of a patient and (e) a governmental agency, said exchange of data being supported by using data format and protocol conversion.

20. A system for processing claim data related to provision of healthcare to a patient, comprising:
    a rules processor for automatically creating rules for use in adaptively processing collated claim data in response to previously identified claim data deficiencies and for processing acquired claim data to identify a condition triggering application of a first set of rules for determining validity of an individual claim element;

a claim data collator for collating individual claim element data for a particular patient for submission to a payer;

a source of a second set of rules including automatically created rules for use in processing collated claim data;

a pre-processor for submitting said collated claim data for automatic trial adjudication by a healthcare provider to determine expected adjudication results including expected reimbursement prior to submission for adjudication by a payer using said second set of rules to validate said collated claim data is in condition for processing to initiate generation of payment; and a claim processor, for submitting said collated claim data to said payer for adjudication by said payer, in response to successful validation by said pre-processor.

21. A system according to claim 20, wherein said rules processor processes an individual claim element for an individual healthcare encounter in response to a record of said individual healthcare encounter being incorporated into said particular patient collated claim data.

22. A system according to claim 21, wherein said pre-processor processes said particular patient collated claim data in response to completion of said particular patient collated claim data.

23. A system according to claim 20, wherein said pre-processor automatically re-submits amended collated claim data for processing using said rules to validate said collated claim data is in condition for processing to initiate generation of payment, said amended collated claim data being received in response to unsuccessful validation using said rules.

24. A system according to claim 20, wherein said second set of rule includes said first set of rules.

25. A system according to claim 20, wherein said first set of rules is for use in editing claim data.

26. A method for processing claim data related to provision of healthcare to a patient, comprising the steps of:

creating rules for use in adaptively processing collated claim data in response to previously identified claim data deficiencies;

processing acquired claim data to identify a condition triggering application of rules for determining validity of an individual claim element;

collating data related to a claim for a particular patient for submission to a payer;

pre-processing collated claim data by performing automatic trial adjudication to determine expected adjudication results including expected reimbursement prior to submission for adjudication by a payer using predetermined and created rules to validate said collated claim data is in condition for processing to initiate generation of payment; and submitting said collated claim data to said payer for adjudication by said payer, in response to successful validation by said pre-processor.

27. A method according to claim 26, including the step of, re-submitting amended collated claim data for processing using said rules to validate said collated claim data is in condition for processing to initiate generation of payment, said amended collated claim data being received in response to unsuccessful validation using said rules.

28. A system for processing claim data related to provision of healthcare to a patient, comprising:

a claim data collator for collating data related to a claim for a particular patient for submission to a payer;

a source of rules for use in processing collated claim data;

a pre-processor for submitting said collated claim data for automatic trial adjudication by a healthcare provider to determine expected adjudication results including expected reimbursement prior to submission for adjudication by a payer using said rules to validate said collated claim data is in condition for processing to initiate generation of payment; and a claim processor, for submitting said collated claim data to said payer for adjudication by said payer, in response to successful validation by said pre-processor wherein said pre-processor obtains a system certification from a payer following successful validation of multiple sets of collated claim data indicating system operation in accordance with payer rules, said certification signifying a threshold level of capability of said system.

* * * * *